(12) United States Patent
Gumm (10) Patent No.: US 8,657,865 B2
(45) Date of Patent: Feb. 25, 2014

(54) CONICAL BALLOON FOR DEPLOYMENT INTO SIDE BRANCH

(75) Inventor: Darrel C. Gumm, Peoria, IL (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 395 days.

(21) Appl. No.: 12/856,375

(22) Filed: Aug. 13, 2010

(65) Prior Publication Data

US 2010/0305681 A1 Dec. 2, 2010

Related U.S. Application Data

(63) Continuation of application No. 11/262,689, filed on Oct. 31, 2005, now Pat. No. 7,776,079.

(51) Int. Cl.
A61F 2/06 (2013.01)

(52) U.S. Cl.
USPC .......................................... 623/1.11; 606/194

(58) Field of Classification Search
USPC .......... 606/194, 195, 108; 623/1.11; 604/284, 604/509
See application file for complete search history.

(56) References Cited

U.S. PATENT DOCUMENTS

| | | | |
|---|---|---|---|
| 5,409,458 A | 4/1995 | Khairkhahan et al. | |
| 5,613,980 A | 3/1997 | Chauhan | |
| 6,017,324 A | 1/2000 | Tu et al. | |
| 6,033,434 A * | 3/2000 | Borghi | 623/1.35 |
| 6,071,285 A * | 6/2000 | Lashinski et al. | 623/1.11 |
| 6,117,117 A | 9/2000 | Mauch | |
| 6,129,738 A * | 10/2000 | Lashinski et al. | 606/194 |
| 6,142,973 A * | 11/2000 | Carleton et al. | 604/96.01 |
| 6,254,593 B1 | 7/2001 | Wilson | |
| 6,409,741 B1 | 6/2002 | Crocker et al. | |
| 6,514,281 B1 | 2/2003 | Blaeser et al. | |
| 6,596,020 B2 | 7/2003 | Vardi et al. | |
| 6,706,062 B2 * | 3/2004 | Vardi et al. | 623/1.15 |
| 6,749,628 B1 | 6/2004 | Callol et al. | |
| 6,780,174 B2 | 8/2004 | Mauch | |
| 6,835,203 B1 | 12/2004 | Vardi et al. | |
| 6,908,477 B2 | 6/2005 | McGuckin, Jr. et al. | |
| 2003/0093109 A1 * | 5/2003 | Mauch | 606/194 |
| 2004/0220606 A1 | 11/2004 | Goshgarian | |
| 2005/0015108 A1 | 1/2005 | Williams et al. | |
| 2005/0060027 A1 * | 3/2005 | Khenansho et al. | 623/1.35 |
| 2005/0102019 A1 | 5/2005 | Yadin | |
| 2007/0208406 A1 * | 9/2007 | Alkhatib et al. | 623/1.11 |
| 2008/0109060 A1 * | 5/2008 | Yadin | 623/1.11 |

FOREIGN PATENT DOCUMENTS

| | | |
|---|---|---|
| EP | 0161863 B1 | 11/1985 |
| EP | 0965311 A2 | 12/1999 |
| WO | 03/105922 A2 | 12/2003 |

* cited by examiner

*Primary Examiner* — S. Thomas Hughes
*Assistant Examiner* — Julie A Szpira
(74) *Attorney, Agent, or Firm* — Seager, Tufte & Wickhem LLC (57) ABSTRACT

A bifurcated catheter assembly has an undeployed state and a deployed state. The assembly comprises a bifurcated inflation shaft defining a shaft inner lumen, a first balloon defining a first balloon lumen, and a second balloon defining a second balloon lumen. The inflation shaft has a first inflation shaft defining a first lumen and a second inflation shaft defining a second lumen. The first balloon defines a first balloon lumen which is in fluid communication with the first lumen. The second balloon defines a second balloon lumen which is in fluid communication with the second lumen. The second balloon has a conical shape.

14 Claims, 6 Drawing Sheets

CONICAL BALLOON FOR DEPLOYMENT INTO SIDE BRANCH

CROSS-REFERENCE TO RELATED APPLICATIONS

This application is a continuation of co-pending U.S. application Ser. No. 11/262,689, filed Oct. 31, 2005, the entire disclosure of which is incorporated herein by reference.

FIELD OF THE INVENTION

In some embodiments this invention relates to implantable medical devices, their manufacture, and methods of use. Some embodiments are directed to delivery systems, such as catheter systems of all types, which are utilized in the delivery of such devices.

BACKGROUND OF THE INVENTION

A stent is a medical device introduced to a body lumen and is well known in the art. Typically, a stent is implanted in a blood vessel at the site of a stenosis or aneurysm endoluminally, i.e., by so-called "minimally invasive techniques" in which the stent in a radially reduced configuration, optionally restrained in a radially compressed configuration by a sheath and/or catheter, is delivered by a stent delivery system or "introducer" to the site where it is required. The introducer may enter the body from an access location outside the body, such as through the patient's skin, or by a "cut down" technique in which the entry blood vessel is exposed by minor surgical means.

Stents and similar devices such as stent, stent-grafts, expandable frameworks, and similar implantable medical devices, are radially expandable endoprostheses which are typically intravascular implants capable of being implanted transluminally and enlarged radially after being introduced percutaneously. Stents may be implanted in a variety of body lumens or vessels such as within the vascular system, urinary tracts, bile ducts, fallopian tubes, coronary vessels, secondary vessels, etc. Stents may be used to reinforce body vessels and to prevent restenosis following angioplasty in the vascular system. They may be self-expanding, expanded by an internal radial force, such as when mounted on a balloon, or a combination of self-expanding and balloon expandable (hybrid expandable).

Stents may be created by methods including cutting or etching a design from a tubular stock, from a flat sheet which is cut or etched and which is subsequently rolled or from one or more interwoven wires or braids.

Within the vasculature it is not uncommon for stenoses to form at a vessel bifurcation. A bifurcation is an area of the vasculature or other portion of the body where a first (or parent) vessel is bifurcated into two or more branch vessels. Where a stenotic lesion or lesions form at such a bifurcation, the lesion(s) can affect only one of the vessels (i.e., either of the branch vessels or the parent vessel) two of the vessels, or all three vessels. Many prior art stents however are not wholly satisfactory for use where the site of desired application of the stent is juxtaposed or extends across a bifurcation in an artery or vein such, for example, as the bifurcation in the mammalian aortic artery into the common iliac arteries.

A variety of catheter types are known which may be used to treat a vessel bifurcation and/or deliver a stent thereto. Catheters having multiple balloons, for example, are shown and described in U.S. Pat. No. 6,780,174 to Mauch, the entire contents of which is herein incorporated by reference.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All U.S. patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention maybe found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

In at least one embodiment a bifurcated catheter assembly, having two balloons, has an undeployed state and a deployed state wherein in a deployed state at least one balloon has a conical shape. The assembly includes a bifurcated inflation shaft defining a shaft inner lumen; the bifurcated inflation shaft can have a first inflation shaft defining a first lumen and a second inflation shaft defining a second lumen. In at least one embodiment, a first balloon defining a first balloon lumen, the first balloon lumen in fluid communication with the first lumen. In at least one embodiment, a second balloon defines a second balloon lumen which is in fluid communication with the second lumen. In at least one embodiment, the second balloon has a working portion disposed about an axis and substantially conical in shape. In at least one embodiment, the diameter of the first end is smaller than the diameter of the second end. The portion there between the first end and the second end can have a diameter that decreases from the diameter of about that of the second end to a diameter of about that of the first end.

In at least one embodiment, the second inflation shaft has an elliptical shape in cross-section.

In at least one embodiment, the second inflation shaft is a hypotube.

In at least one embodiment, the second balloon is disposed about less than the entire circumference of the hypotube.

In at least one embodiment, the second balloon has a conical shape with a substantially right angle.

In at least one embodiment, the second inflation shaft has an expandable end which is a balloon.

In at least one embodiment, the second balloon is engaged to the first balloon. In at least one embodiment the second balloon is welded to the first balloon through heat, chemical or adhesive welding. In at least one embodiment the second balloon is mechanically engaged to the first balloon.

In at least one embodiment, the second balloon includes a wire lumen in the undeployed state.

In at least one embodiment, a first portion of the second balloon folds over on a second portion of the second balloon to form a guide wire lumen in the undeployed state. In at least one embodiment, in the deployed state the folded first portion and second portion forming the guidewire lumen unfold such that the guidewire lumen is unformed.

In at least one embodiment, a guidewire within the guidewire lumen in the undeployed state is released in the deployed state.

In at least one embodiment, the second balloon is in fluid communication with the inner lumen such that fluid pressure within the inner lumen expands the first balloon before the second balloon.

In at least one embodiment, a guidewire is disposed within the hypotube.

In at least one embodiment, the second balloon has a tip with a diameter of about 2 mm and a base with a diameter of about 3.5 mm.

In at least one embodiment, a bifurcated stent is disposed about the first balloon and second balloon.

In at least one embodiment, the stent has petals which are radially disposed about the second balloon.

In at least one embodiment, the stent has petals such that expansion of the second balloon extends the petals in a direction oblique to the longitudinal axis of the stent.

In at least one embodiment, the working portion of the second balloon is conical with a base portion and a tip portion. The base portion is at least partially disposed about the second inflation shaft and the tip portion is more distal to the second inflation shaft than the base portion. The working portion of the second balloon can have a variable compliance such that the base portion is more compliant than the tip portion.

In at least one embodiment, the stent has a hood having a proximal end and a distal end. In at least one embodiment, the hood can be disposed about the second balloon such that expansion of the second balloon forces the hood outward in a direction oblique to the longitudinal axis.

In at least one embodiment in the expanded state, the hood portion can form an obtuse angle with the primary stent body at the proximal end and an acute angle with the primary stent body at the distal end.

In at least one embodiment a bifurcated catheter assembly comprises a first inflation shaft defining a first inner lumen, a second inflation shaft defining a second inner lumen having an elliptical shape, a first balloon, and a second balloon. The first balloon is disposed about the first inflation shaft and defines a first balloon lumen which is in fluid communication with the first inner lumen. The second balloon is disposed about the second inflation shaft and defines a second balloon lumen which is in fluid communication with the second inner lumen.

In at least one embodiment, the first inflation shaft and the second inflation shaft are located at the distal end of the bifurcated catheter assembly. In at least one embodiment, the first and second inflation shafts intersect to form a single shaft that extends to the proximal end of the catheter assembly.

In at least one embodiment, the first balloon can have a working body portion that is substantially cylindrical and which can have a cone portion at each end, and the second balloon can have a working portion that is substantially conical in shape. In at least one embodiment, the conical shaped balloon can have a wider base portion that is connected to the second inner shaft and can have a smaller peak portion of the balloon opposite the base portion.

In at least one embodiment, a method of deploying a stent at a bifurcation can include 1) providing a bifurcated catheter assembly as described above, 2) disposing a stent having an expandable side branch portion about the first balloon and the second balloon wherein the expandable side branch portion is disposed about the second balloon, 3) advancing a bifurcated catheter assembly and stent to the bifurcation, 4) inflating the first balloon, and 5) inflating the second balloon such that the second balloon expands the side branch portion into a second lumen of the bifurcation.

In at least one embodiment, the side branch portion is a plurality of petals.

In at least one embodiment, the side branch portion is a hood.

These and other embodiments which characterize the invention are pointed out with particularity in the claims annexed hereto and forming a part hereof. However, for further understanding of the invention, its advantages and objectives obtained by its use, reference should be made to the drawings which form a further part hereof and the accompanying descriptive matter, in which there is illustrated and described embodiments of the invention.

BRIEF DESCRIPTION OF THE SEVERAL VIEWS OF THE DRAWINGS

A detailed description of the invention is hereafter described with specific reference being made to the drawings.

DETAILED DESCRIPTION OF THE INVENTION

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Figure 1A:
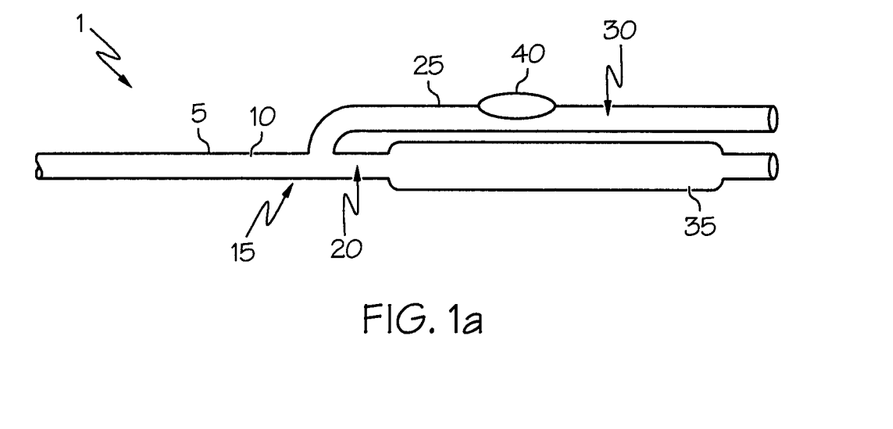
FIG. 1 is a side view of an embodied unexpanded catheter assembly.
Figure 1B:
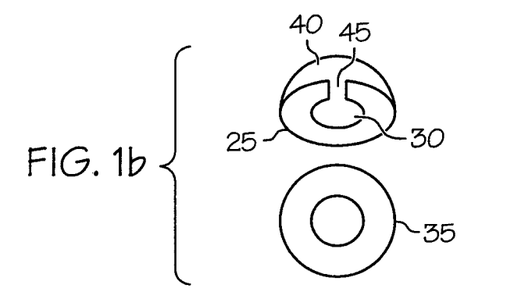
FIG. 1b is a cross-sectional view of an unexpanded catheter assembly.

In FIG. 1a an uninflated distal end of a bifurcated catheter 1 is shown. The catheter has an inflation shaft 5 with an inner lumen 10. The inflation shaft branches into a first inflation shaft 15 having a first lumen 20 and a second inflation shaft 25 having a second lumen 30. A first balloon 35 is disposed about the first shaft and a second balloon 40 is disposed about the second shaft. In at least one embodiment, the second inflation shaft is a hypotube and the second balloon 40 is disposed only partly about the circumference of the hypotube. In some embodiments, the second balloon is only attached to a small portion of the circumference of the second shaft/hypotube. In some embodiments there are two inflation lumens throughout the catheter 1 such that the first balloon has a dedicated inflation shaft and the second balloon 40 has a dedicated inflation shaft. The balloons 35, 40 can be inflated at different times or rates when each has a dedicated inflation shaft. A hole 45 as shown in FIG. 1b in the second shaft/hypotube 25 can provide fluid communication between the second lumen and the balloon lumen of the second balloon 40. In some embodiments, the second shaft 25 and/or second lumen can be elliptically shaped such that when enough fluid pressure is applied within the inner lumen to inflate the first balloon 35, additional pressure may be necessary to inflate the second balloon 40 when the second lumen is elliptically shaped. The elliptical shape of the second lumen resists fluid movement more than a second lumen having an identically sized circular cross-sectional area. Other shapes and sizes can be used as well in order to inflate the first balloon before the second balloon.

Figure 2A:
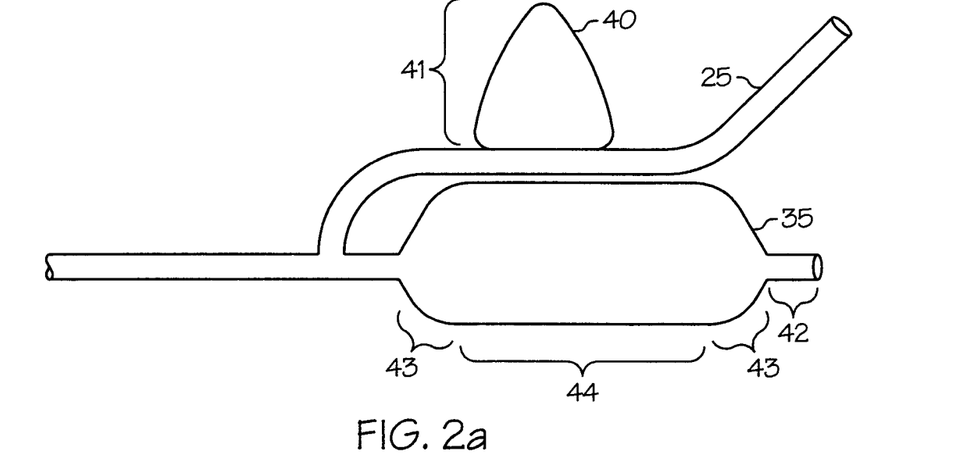
FIG. 2a is a side view of an embodied expanded catheter assembly.
Figure 2B:
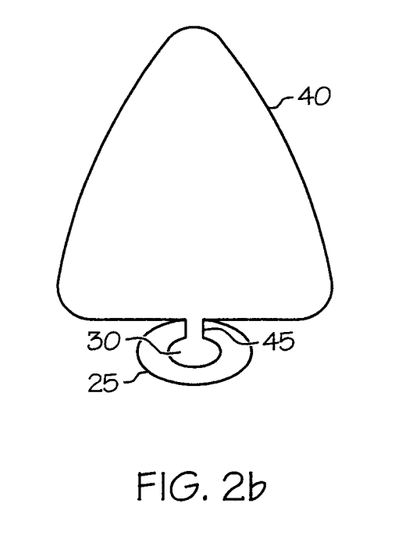
FIG. 2b is a cross-sectional view of an embodied expanded catheter assembly.

In FIG. 2a the balloons are in an expanded condition. The second balloon 40 has a working portion 41 which is conical in shape as shown. The first balloon 35 which has a waist portion 42, a cone portion 43, and a working portion 44. The working portion of the first balloon 35 is cylindrical in shape. The working portion can be characterized as the portion of the balloon which engages and expands the stent when the balloon is inflated. In the expanded state the conical balloon 40 is attached to only a portion of the second shaft 25 as shown in FIG. 2b. In some embodiments the conical balloon 40 rests on the second shaft 25. In some embodiments the second shaft 25 is connected to first balloon 35 through connection means such as an adhesive or weld.

In at least one embodiment, the second balloon is constructed with variable compliance such that the base portion (proximal most portion relative to the second shaft 25) of the second balloon is highly compliant and the distal portion or tip is highly non-compliant. This can create a balloon that will inflate from the proximal portion to the distal portion rather than uniformly along the length. Thus, the side petal of a stent (e.g., a stent as shown in FIG. 6) can be deployed into the side branch in a more uniform manner.

Figure 3:
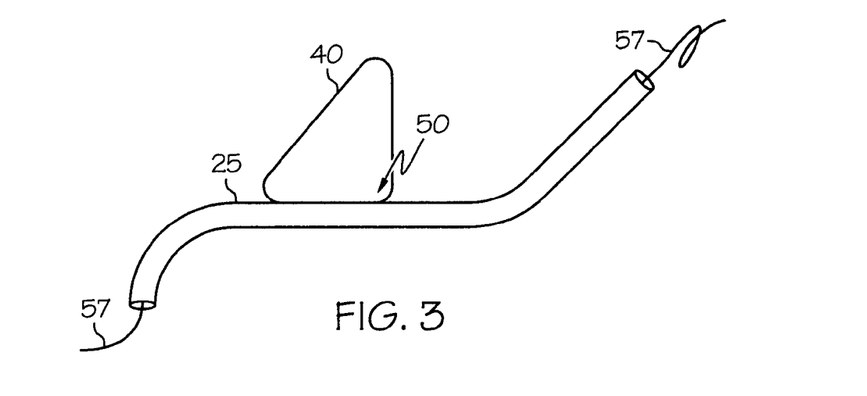
FIG. 3 is a side view of an embodied catheter balloon.

The conical balloon 40 can also have a substantially right angle 50 as shown in FIG. 3. When a stent 55 (as shown in FIGS. 6-7), having petals which form a side branch in a bifurcation, is disposed about the balloons 35/40, the right angled conical construction may deploy the petals more favorably such that a natural ostium is formed. The second shaft 25 can also serve as a guidewire shaft for a guidewire 57.

Figure 4A:
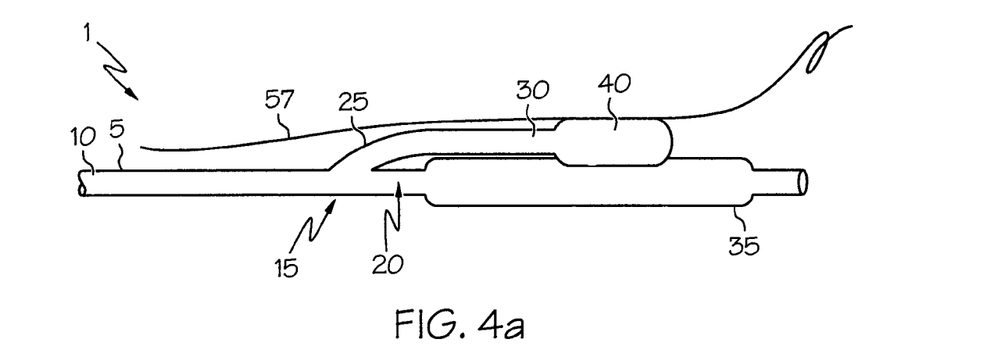
FIG. 4a is a side view of an embodied unexpanded catheter assembly.
Figure 4B:
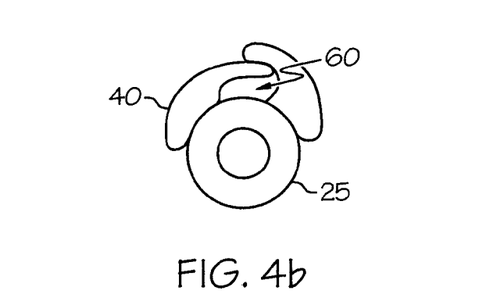
FIG. 4b is a cross-sectional view of an embodied unexpanded catheter assembly.
Figure 5:
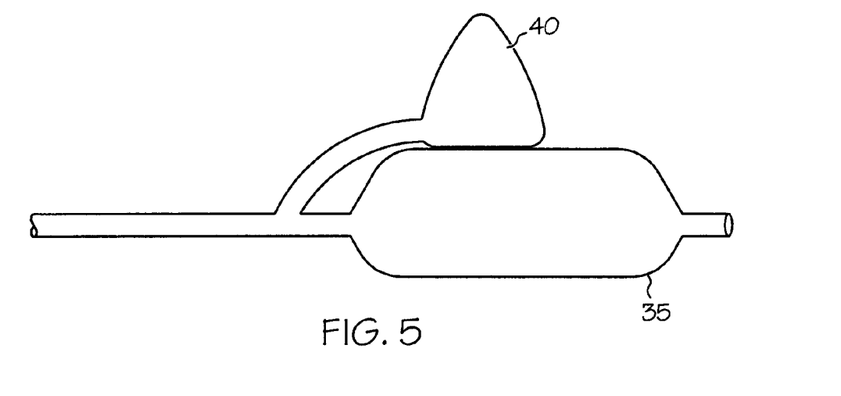
FIG. 5 is a side view of an embodied expanded catheter assembly.

In some embodiments, the balloon and second shaft are of one piece construction. In FIG. 4a an uninflated distal end of a bifurcated catheter 1 is shown wherein the conical balloon 40 is an expandable end of the second shaft 25. On embodiment of a portion of conical balloon 40 is shown in FIG. 4b, the balloon 40 may fold over on itself to form a guidewire lumen 60. The lumen can be formed with or without a stent. In the expanded state as shown in FIG. 5 the guidewire 57 (not shown) is released. In some embodiments the conical balloon is used to only initially open the side branch and another balloon is used to perform the final expansion of the side branch. This mechanism shortens the final side branch expansion in that the bifurcated balloon system need not first be removed and two additional balloons inserted.

Figure 6:
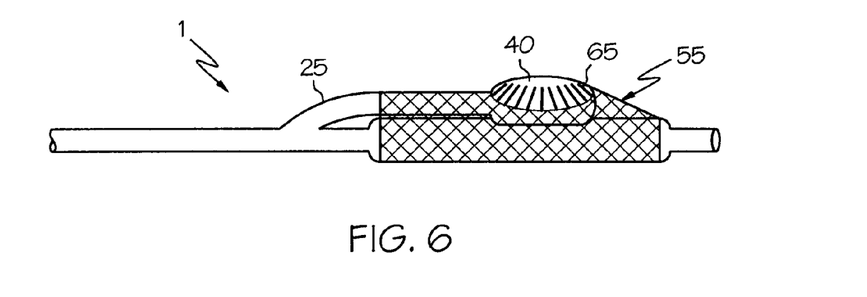
FIG. 6 is a side view of an embodied unexpanded catheter assembly with a stent.
Figure 7:
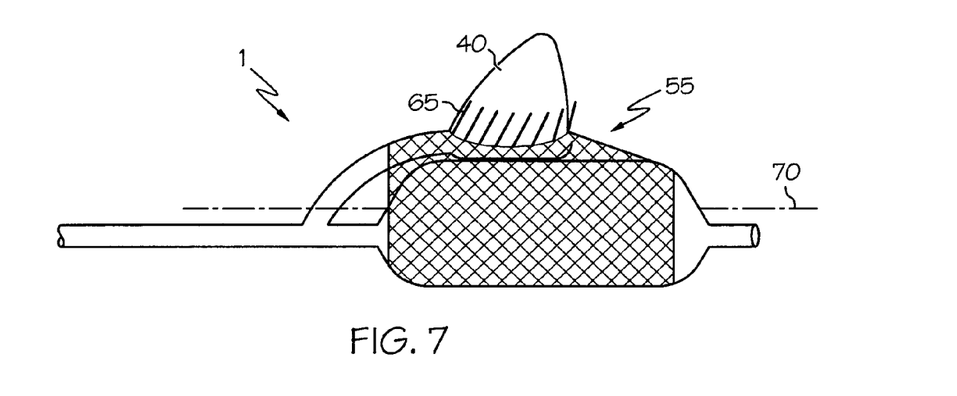
FIG. 7 is a side view of an embodied expanded catheter assembly with a stent.

In FIGS. 6-7 a stent 55 having petal portions 65 is disposed about the distal end of the catheter 1. In the unexpanded state the petals 65 can lie within the unexpanded wall structure of the stent 55. While the petals may extend in any number of designs, in some embodiments the petals extend in a substantially longitudinal direction relative to the second shaft 25 when in the unexpanded state. In other embodiments the petals point substantially radially toward a center portion of the second lumen when in the unexpanded state. In some embodiments the petals are a part of a crown structure which defines the side branch opening of the stent and provides for extension through the ostium of the side branch vessel. Upon expansion as shown in FIG. 7 the petals extend in a direction oblique to the longitudinal axis 70 of the first lumen of the stent 55. The conical balloon 40, as shown, has a right angle configuration which in some medical applications orients the petals more favorably in the second lumen of a bifurcation.

Figure 8:
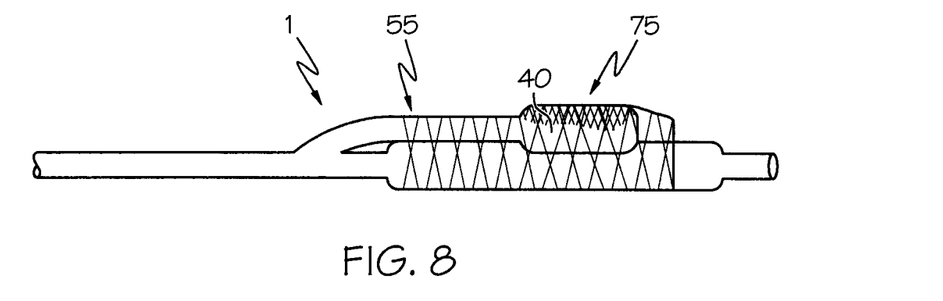
FIG. 8 is a side view of an embodied unexpanded catheter assembly with a stent.
Figure 9:
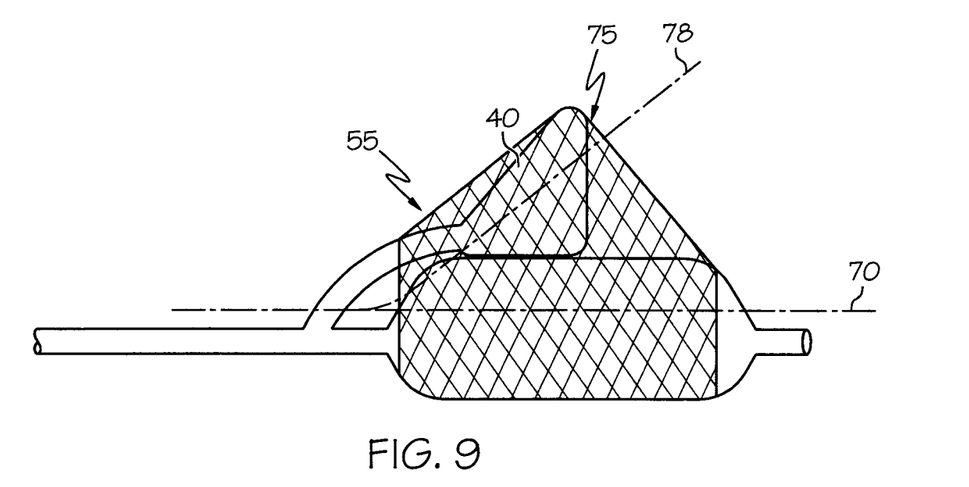
FIG. 9 is a side view of an embodied expanded catheter assembly with a stent.
Figure 10:
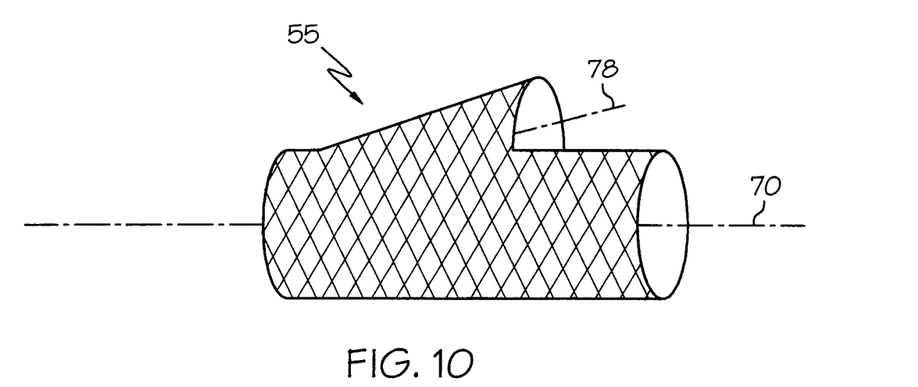
FIG. 10 is a perspective side view of an embodied expanded stent.

In FIGS. 8-10 a stent 55 having a hood portion 75 is disposed about the distal end of the catheter 1. In at least one embodiment, in the unexpanded state the hood 75 can lie within the unexpanded wall structure of the stent 55. The hood consists of interconnecting members (e.g., struts) that may or may not have the substantially same configuration as that of the rest of the stent. In some embodiments the proximal end of the hood is attached to the rest of the stent 55 and the distal end of the hood 75 is not directly attached to the rest of the stent. Configured as such, the hood can be expanded to form a side passage having a longitudinal axis oblique to the longitudinal axis of the rest of the stent. As shown here the hood 75 has a visually different appearance from the rest of the stent 55 in the unexpanded state. The hood portion 75 may be made of the same or different material than that of the rest of the stent. In some embodiments the hood is formed similarly to the rest of the stent, but is capable of being expanded to a greater extent than the rest of the stent. In some embodiments in the unexpanded state, the hood 75 consists of a greater density of material than does the other portions of the stent 55. The greater density of material of the hood allows for greater expansion of the hood. In some embodiments upon expansion as shown in FIGS. 9-10, the hood 75 expands out to provide coverage to the ostium of the sidebranch vessel. The hood portion 75 has a longitudinal axis 78. In some embodiments the hood longitudinal axis 78 forms an acute angle with longitudinal axis 70 of the rest of the stent 55. In some embodiments, another stent or stent graft can extend through the lumen of the hood portion in order to extend the area of coverage and support. As shown, the hood portion 75 extends in a direction oblique to the longitudinal axis 70 of the first lumen of the stent 55. The conical balloon 40, as shown in FIG. 9, has a right angle configuration which in some applications orients the hood more favorably in the second lumen of a bifurcation. It should be noted that the conical balloon need not have a right angle in any of the figures in which a right angle is shown.

Figure 11:
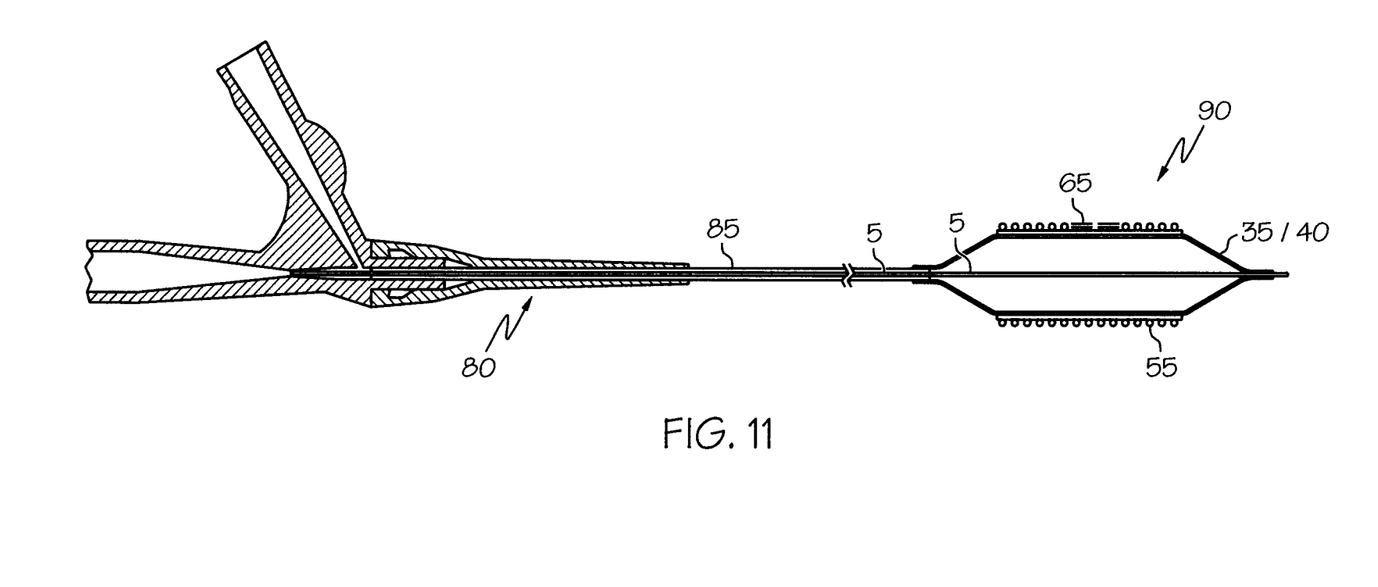
FIG. 11 is a cross-sectional side view of a stent delivery apparatus.

As shown in FIG. 11, the various embodied conical balloons 40 can be a part of a stent delivery system 80 having an inflation shaft 5 with or without the outer catheter shaft 85 and having stent receiving region 90. The stent 55 can be disposed about balloons 35/40. While only a single balloon is shown here, the multiple balloons as described in this application can be used. One balloon can be used to expand the primary body portion of stent 55 while another balloon is used for expanding the petals 65 or the hood 75.

In some embodiments the stent, the delivery system or other portion of the assembly may include one or more areas, bands, coatings, members, etc. that is (are) detectable by imaging modalities such as X-Ray, MRI, ultrasound, etc. In some embodiments at least a portion of the stent and/or adjacent assembly is at least partially radiopaque.

In some embodiments the at least a portion of the stent is configured to include one or more mechanisms for the delivery of a therapeutic agent. The agent will be in the form of a coating or other layer (or layers) of material in any suitable form placed on a surface region of the stent, which is adapted to be released at the site of the stent's implantation or areas adjacent thereto. Alternately, the therapeutic agent can reside in a reservoir formed within or on the stent using suitable configurations or arrangements.

A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS), polyethylene oxide, silicone rubber and/or any other suitable substrate.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g., each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

I claim:

1. A bifurcated catheter assembly having an undeployed state and a deployed state, the assembly comprising:
   a shaft including a distal region and a proximal region, wherein the distal region of the shaft includes a first branch and a second branch, the first branch defining a first inflation lumen and the second branch defining a second inflation lumen;
   a first balloon disposed about a portion of the first branch and defining a first balloon lumen, the first balloon lumen in fluid communication with the first inflation lumen; and
   a second balloon disposed about a portion of the second branch and defining a second balloon lumen, the second balloon lumen in fluid communication with the second inflation lumen, the second balloon including a first end, a second end, and a length extending therebetween, the second balloon being substantially conical shaped from the first end to the second end when inflated, the first end having a first diameter and being positioned radially furthest from the first balloon when the second balloon is expanded, and the second end having a second diameter and being positioned radially closest to the first balloon when the second balloon is expanded, the first diameter being smaller than the second diameter, the portion therebetween having a diameter that decreases gradually along the entire length from the second diameter to the first diameter.

2. The bifurcated catheter assembly of claim 1 wherein the second balloon extends radially outward relative to the second shaft.

3. The bifurcated catheter assembly of claim 1 wherein the second shaft has an elliptical shape in cross-section.

4. The bifurcated catheter assembly of claim 1 wherein the second balloon defines the end of the second shaft.

5. The bifurcated catheter assembly of claim 1 wherein the second balloon is secured to the first balloon.

6. The bifurcated catheter assembly of claim 1 wherein in the undeployed state a first portion of the second balloon folds over on a second portion of the second balloon and forms a guidewire lumen, in the deployed state the folded first portion unfolds such that the guidewire lumen is unformed.

7. The bifurcated catheter assembly of claim 6 further comprising a guidewire disposed within the guidewire lumen in the undeployed state, the guidewire released in the deployed state.

8. The bifurcated catheter assembly of claim 1 wherein the first and second inflation lumens are in fluid communication with each other and the second balloon is constructed such that the first balloon expands before the second balloon expands.

9. The bifurcated catheter assembly of claim 1 wherein the assembly includes a stent having a primary stent body and longitudinal axis parallel to the central axis of the first balloon, wherein when the second balloon is deflated, the primary stent body is disposed about the first end of the second balloon, and the second end of the second balloon, and when the second balloon is inflated, the primary stent body is disposed about the second end of the second balloon and the first end of the second balloon extends through a side opening of the primary stent body.

10. The bifurcated catheter assembly of claim 9 wherein the stent has petals disposed about the second balloon such that expansion of the second balloon forces the petals outward in a direction oblique to the longitudinal axis.

11. The bifurcated catheter assembly of claim 9 wherein the stent has a hood having a proximal end and a distal end, the hood disposed about the second balloon such that expansion of the second balloon forces the hood outward in a direction oblique to the longitudinal axis.

12. The bifurcated catheter assembly of claim 11 wherein in the expanded state the hood portion forms an obtuse angle with the primary stent body at the proximal end and an acute angle with the primary stent body at the distal end.

13. A bifurcated catheter assembly having an undeployed state and a deployed state, the assembly comprising:
   a first shaft defining a first inflation lumen;
   a second shaft defining a second inflation lumen;
   a first balloon disposed about the first shaft and defining a first balloon lumen, the first balloon lumen in fluid communication with the first inflation lumen;

a second balloon disposed about the second shaft and defining a second balloon lumen, the second balloon lumen in fluid communication with the second inflation lumen, wherein the first and second balloons are in fluid communication with each other, the second balloon including a first end, a second end, and a length extending therebetween; and wherein, when inflated, the first balloon has a first working body portion that is substantially cylindrical in shape and, when inflated, the second balloon has a second working body that is substantially conical in shape from the first end to the second end, the second balloon extending radially outward from the first balloon when the second balloon is inflated, wherein when inflated, the first end of the second balloon has a first diameter and the second end has a second diameter, the first diameter being smaller than the second diameter, the portion therebetween having a diameter that decreases gradually along the entire length from the second diameter to the first diameter; and a stent disposed about the first balloon and the second balloon, the stent having a primary stent body, wherein a portion of the second balloon extends through the primary stent body when the second balloon is inflated.

14. The bifurcated catheter assembly of claim 13 having a proximal end portion and a distal end portion, the first shaft and the second shaft located at the distal end portion, the first shaft and the second shaft intersecting to form a single shaft at a location proximal of the first and second balloons and distal of the proximal end portion, wherein the single shaft extends to the proximal end portion of the catheter assembly.

* * * * *